United States Patent [19]

Seki et al.

[11] Patent Number: 4,505,739

[45] Date of Patent: Mar. 19, 1985

[54] HERBICIDAL 5-T-BUTYL-3-(N-ALKANOYLAMINO)-PYRAZOLES

[75] Inventors: Nansho Seki; Yuki Yamaguchi; Yukihiro Nakamura; Hiroshi Kubo; Tetsuo Tsuruya, all of Tokyo, Japan

[73] Assignee: Showa Denko Kabushiki Kaisha, Tokyo, Japan

[21] Appl. No.: 368,232

[22] Filed: Jan. 13, 1982

[30] Foreign Application Priority Data

Apr. 13, 1981 [JP] Japan .................................. 56-54321

[51] Int. Cl.³ .................... A01N 43/56; C07D 231/40
[52] U.S. Cl. .......................................... 71/92; 548/362
[58] Field of Search ............................. 548/362; 71/92

[56] References Cited

U.S. PATENT DOCUMENTS

| | | | |
|---|---|---|---|
| 3,754,887 | 8/1973 | Brantley | 71/92 |
| 3,920,690 | 11/1975 | Harrington et al. | 71/92 |
| 3,920,693 | 11/1975 | Ege | 548/362 |
| 4,146,632 | 3/1979 | Hofer et al. | 424/273 P |
| 4,260,775 | 4/1981 | Plath et al. | 548/362 |

FOREIGN PATENT DOCUMENTS 260230 2/1968 Austria .
55-89293 5/1980 Japan .

OTHER PUBLICATIONS

Dorn et al., Annalen 1967, vol. 707, pp. 141-146.
Fomum et al., Tetrahedron Letters 1975, No. 13, pp. 1101-1104.

Primary Examiner—Henry R. Jiles
Assistant Examiner—Kurt G. Briscoe
Attorney, Agent, or Firm—Sughrue, Mion, Zinn, Macpeak, and Seas

[57] ABSTRACT

A novel pyrazole derivative represented by the formula [I]:

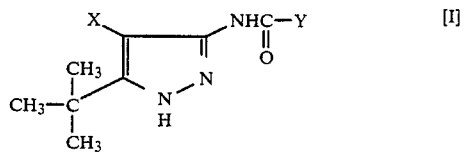

wherein X and Y are defined in the specification, which has a herbicidal activity, is disclosed. A process for preparing the pyrazole derivative of the formula [I] is also disclosed. A herbicide containing as an active ingredient the pyrazole derivative of the formula [I] is further disclosed.

16 Claims, No Drawings

HERBICIDAL 5-T-BUTYL-3-(N-ALKANOYLAMINO)PYRAZOLES

This invention relates to a novel pyrazole derivatives, in particular, a 5-t-butyl-3-acylaminopyrazole derivative represented by the formula [I]:

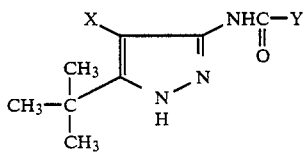

[I]

wherein X is a hydrogen atom, a chlorine atom, a bromine atom or a nitro group, and Y is a hydrogen atom; a straight or branched chain alkyl group having 1 to 10 carbon atoms, which may be substituted with halogen atoms or an alkoxy group; a straight, or branched chain alkenyl group having 2 to 8 carbon atoms; a cycloalkyl group having 3 to 6 carbon atoms, which may be substituted with halogen atoms or lower alkyl groups; an aralkyl group; or a

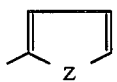

group wherein Z is an oxygen atom or a sulfur atom. This invention also relates to a process for preparing the compound of the formula [I]. This invention further relates to a herbicide containing the compound of the formula [I] as an active ingredient.

With respect to the compound of the formula [I], there is a possible tautomer other than the compound represented by the formula [I] as illustrated below.

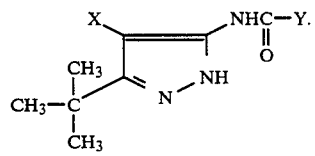

However, in the following explanation this tautomer is representatively expressed by the formula [I].

The compound of the formula [I] is characterized by having a t-butyl group at the 5-position of the pyrazole ring thereof, such characteristic having a great meaning in herbicidal activity.

The compound of the formula [I] exhibits a strong herbicidal activity against a wide range of weeds, and if it is applied to the weeds in an amount of from 0.5 to 10 Kg/ha before the emergence of the weeds or at the early growth stage thereof, it can control a wide range of the weeds.

In other words, when the application amount of the compound of this invention is controlled, or an appropriate application method is employed, it can selectively control various weeds which grow in cultivation fields for crops, such as corn, potato, sugar beet, peanut, soybeans, sunflower, barley, wheat, sorghum, cotton, fruits and the like.

Typical compounds according to this invention are shown in Table 1 below.

TABLE I

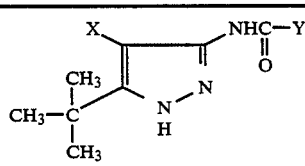

| Compound No. | X | Y | Melting Point (°C.) | Solvent** | NMR Analysis Data* H—NMR [δ value (ppm)] |
|---|---|---|---|---|---|
| 1 | H | —H | 204–206 | A | 1.25(9H, s), 6.23(1H, s), 8.13(1H, s), 10.3(1H, br), 11.5–12.3(1H, br) |
| 2 | H | —CH₃ | 194–195 | A | 1.24(9H, s), 1.98(3H, s), 6.23(1H, s), 10.1(1H, br), 11.5–12(1H, br) |
| 3 | Cl | —CH₃ | 240–242 | A | 1.34(9H, s), 1.99(3H, s), 9–10(1H, br), 12–13(1H, br) |
| 4 | Br | —CH₃ | 234–235 | A | 1.30(9H, s), 1.98(3H, s), 9.5(1H, br), 12–13(1H, br) |
| 5 | NO₂ | —CH₃ | 174–175 | A | 1.37(9H, s), 2.19(3H, s) 10–10.5(1H, br) |
| 6 | H | —C₂H₅ | 228–229 | A | 1.07(3H, t, J=7), 1.25(9H, s), 2.29(2H, q, J=7), 6.27(1H, br), 10.1(1H, br), 11–12(1H, br) |
| 7 | Cl | —C₂H₅ | 136–137 | A | 1.04(3H, t, J=7), 1.34(9H, s), 2.27(2H, q, J=7), 9.5(1H, br) 12.5(1H, br) |
| 8 | Br | —C₂H₅ | 136–138 | A | 1.04(3H, t, J=7), 1.34(9H, s), 2.27(2H, q, J=7), 9.43(1H, br), 12.2–12.7(1H, br) |
| 9 | NO₂ | —C₂H₅ | 161–162 | B | 1.29(3H, t, J=7), 1.33(9H, s), 2.61(2H, q, J=7), 9.8–10.2(1H, br) |
| 10 | H | —C₃H₇—n | 202–203 | A | 0.89(3H, t, J=7), 1.25(9H, s), 1.2–1.9(2H, m), 2.25(2H, t, J=7) 6.26(1H, s), 10.1(1H, br), 11–12(1H, br) |

TABLE I-continued

Structure:
- Pyrazole ring with substituents
- X at 4-position
- NHC(=O)—Y at 3-position
- (CH$_3$)$_3$C— (tert-butyl) at 5-position
- NH at 1-position

| Compound No. | X | Y | Melting Point (°C.) | Solvent** | H—NMR [δ value (ppm)] |
|---|---|---|---|---|---|
| 11 | H | —C$_3$H$_7$—iso | 259–261 | A | 1.05(6H, d, J=7), 1.24(9H, s), 2–3(1H, m, J=7), 6.26(1H, s), 10.1(1H, br), 11.5–12.5(1H, br) |
| 12 | H | —C$_4$H$_9$—n | 158–159 | A | 0.88(3H, t, J=7), 1.26(9H, s), 1–2(4H, m), 2.25(2H, t, J=7), 6.24(1H, s), 10.1(1H, br), 11.6–12.1(1H, br) |
| 13 | H | —C$_4$H$_9$—iso | 201–202 | A | 0.91(6H, d), 1.24(9H, s), 1.8–2.4(3H, br), 6.28(1H, s), 10.1(1H, br), 11.95(1H, br) |
| 14 | H | —C$_4$H$_9$—sec | 203–204 | A | 0.83(3H, t, J=7), 1.04(3H, d, J=7), 1.25(9H, s), 1–1.8(2H, m), 2–2.5(1H, m), 6.30(1H, s), 10.1(1H, br), 11.6–12.1(1H, br) |
| 15 | H | —C$_4$H$_9$—tert | 209–210 | A | 1.18(9H, s), 1.25(9H, s), 6.22(1H, s), 9.6(1H, br), 11.4(1H, br) |
| 16 | Cl | —C$_4$H$_9$—tert | 156–158 | A | 1.19(9H, s), 1.32(9H, s), 9.0(1H, br), 12–13(1H, br) |
| 17 | H | —C(CH$_3$)$_2$C$_2$H$_5$ | 190–191 | B | 0.88(3H, t, J=7), 1.24(6H, s), 1.29(9H, s), 1.63(2H, q, J=7), 6.55(1H, s), 8.3(1H, br), 9–10(1H, br) |
| 18 | H | —C(CH$_3$)$_2$C$_3$H$_7$—iso | 181–182 | B | 0.89(6H, d, J=7), 1.18(6H, s), 1.30(9H, s), 1.6–2.4(1H, m), 6.54(1H, s), 8.2(1H, br), 10–11(1H, br) |
| 19 | H | —C(CH$_3$)$_2$C$_3$H$_7$—n | 157–158 | B | 0.97(3H, t), 1.24(6H, s), 1.27(9H, s), 1–2(4H, m), 6.57(1H, s), 8.2–8.5(1H, br), 10.4–11.0(1H, br) |
| 20 | H | —CH=CH$_2$ | 180–182 | A | 1.26(9H, s), 5.5–6.5(4H, m), 10.4(1H, br), 11.5–12.5(1H, br) |
| 21 | H | —C(CH$_3$)=CH$_2$ | 181–182 | A | 1.26(9H, s), 1.91(3H, s), 5.41(1H, s), 5.80(1H, s), 6.27(1H, s), 10.1(1H, br), 11.7–12.2(1H, br) |
| 22 | H | —CH=CHCH$_3$ | 218–219 | A | 1.27(9H, s), 1.83(3H, d, J=7), 6.4(1H, s), 6–7(2H, br), 10.2(1H, br), 11.5–12.1(1H, br) |
| 23 | H | —CH$_2$—CH=CH$_2$ | 197–199 | A | 1.24(9H, s), 3.08(2H, d), 4.9–5.4(2H, m), 5.5–6.4(1H, m), 6.27(1H, s) |
| 24 | H | —CH=C(CH$_3$)—CH$_3$ | 215–216 | A | 1.26(9H, s), 1.82(3H, s), 2.14(3H, s), 5.9(1H, br), 6.31(1H, s), 10.2(1H, br), 11–12.5(1H, br) |
| 25 | H | —C(CH$_3$)=CHCH$_3$ | 175–176 | B | 1.32(9H, s), 1.7–2.0(6H, m), 6.3–6.8(1H, m), 6.56(1H, s), 8.2–8.6(1H, br), 9–9.5(1H, br) |
| 26 | H | —C(CH$_3$)$_2$CH$_2$.CH=CH$_2$ | 150–151 | B | 1.27(6H, s), 1.30(9H, s), 2.36(2H, d), 4.8–6.3(3H, m), 6.55(1H, s), 8.2(1H, br), 9.5–10(1H, br) |
| 27 | H | —CH(cyclopropyl) (CH—CH$_2$—CH$_2$) | 240–241 | A | 0.5–0.9(4H, m), 1.23(9H, s), 1.5–2.1(1H, m), 6.24(1H, s), 10.4(1H, br), 11.9(1H, br) |
| 28 | H | cyclobutyl (with H) | 225–226 | A | 1.25(9H, s), 1.5–2.5(6H, m), 2.8–3.6(1H, m), 6.30(1H, s), 10.0(1H, br), 11.8–12.1(1H, br) |

TABLE I-continued structure: pyrazole with X at 4-position, (CH3)3C- at 5-position, NHC(=O)-Y at 3-position, NH at 1-position

| Compound No. | X | Y | Melting Point (°C.) | Solvent** | H—NMR [δ value (ppm)] |
|---|---|---|---|---|---|
| 29 | H | cyclopentyl (—C5H9) | 208–209 | A | 1.24(9H, s), 1.6–2.0(8H, m), 2.4–3.1(1H, m), 6.28(1H, s), 10.1(1H, br), 11.7–12.1(1H, br) |
| 30 | H | 2,2-dimethylcyclopropyl | 216–217 | A | 1.13(6H, s), 1.26(9H, s) 0.5–2.0(3H, m), 6.28(1H, s), 10.3(1H, br), 11.9(1H, br) |
| 31 | H | —CH2Cl | 188–190 | A | 1.24(9H, s), 4.19(2H, s), 6.27(1H, s), 10.6(1H, s), 11.5–12.5(1H, br) |
| 32 | H | —CHCl2 | 224–225 | A | 1.27(9H, s), 6.34(1H, s), 6.55(1H, s), 11.0(1H, br), 12.3(1H, br) |
| 33 | H | —CCl3 | 195–196 | A | 1.28(9H, s), 6.25(1H, s), 11.2(1H, br), 12.4(1H, br) |
| 34 | H | —CF3 | 192–193 | B | 1.35(9H, s), 6.66(1H, s), 10–11(1H, br) |
| 35 | H | —CH2CH2Cl | 171–172 | A | 1.25(9H, s), 2.47(2H, t, J=7), 3.85(2H, t, J=7), 6.29(1H, s), 10.4(1H, br), 11.7–12.3(1H, br) |
| 36 | H | —CHClCH3 | 217–218 | A | 1.25(9H, s), 1.57(3H, d, J=7), 4.71(1H, q, J=7), 6.30(1H, s), 11.6(1H, br), 12.1(1H, br) |
| 37 | H | 2,2-dichlorocyclopropyl | 262–264 | A | 1.26(9H, s), 1.8–2.2(2H, d), 2.7–3.1(1H, m), 6.28(1H, s), 10.9(1H, br), 12.1(1H, br) |
| 38 | H | —C(CH3)2OCH3 | 175–176 | B | 1.31(9H, s), 1.49(6H, s), 3.33(3H, s), 6.65(1H, s), 10.1–10.8(1H, br), 11.3(1H, br) |
| 39 | H | —C(CH3)2—O—C2H5 | 168–169 | B | 1.20(3H, t, J=7), 1.31(9H, s), 1.49(6H, s), 3.56(2H, q, J=7), 6.64(1H, s), 10.2–10.7(1H, br), 11.3(1H, br) |
| 40 | H | —CH(CH3)—C6H5 | 230–231 | A | 1.23(9H, s), 1.37(3H, d), 3.87(1H, q), 6.27(1H, s), 7.0–7.5(5H, ar), 10.4(1H, br), 11.8–12.2(1H, br) |
| 41 | H | —CH2—C6H5 | 186–187 | A | 1.24(9H, s), 3.62(2H, s), 6.29(1H, s), 7.3(5H, ar), 10.5(1H, br) |
| 42 | H | 2-furyl | 223–224 | A | 1.28(9H, s), 6.26(1H, s), 6.5–8(3H, ar), 10.5(1H, br), 12.1(1H, br) |
| 43 | H | 2-thienyl | 215–216 | A | 1.28(9H, s), 6.37(1H, s), 7.0–8.3(3H, ar), 10.75(1H, br) 12.14(1H, br) |

*The NMR analysis was carried out in DMSO or CDCl3 at 60 MHz in which tetramethylsilane was used as an internal standard, and symbols of s, d, t, q, m, br, ar and J stand for singlet, doublet, triplet, quartet, multiplet, broad peak, aromatic protons and coupling constant.
**A means d6-DMSO and B means CDCl3, respectively.

The compound of the formula [I] can be prepared as follows:

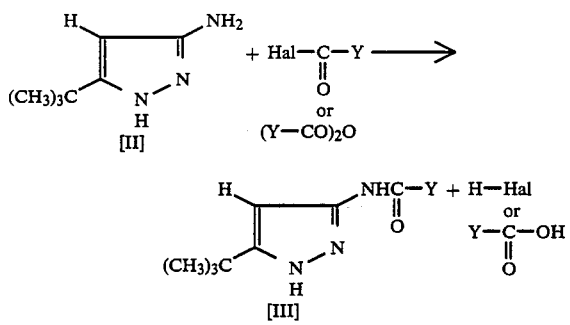

The compound of the formula [III] can be prepared from 5-t-butyl 3-aminopyrazole [II] and an acid halide or an acid anhydride. Where Y is a hydrogen atom, the desired product can be prepared by using formic acid. This reaction is carried out by dropwise adding the acid halide, acid anhydride or formic acid to the aminopyrazole dissolved in a solvent. Although the reaction may proceed in the absence of a base, in order to carry out it under a mild condition, it is preferred to use an organic or inorganic base as a promotor. Any solvent which is stable under the reaction condition and does not react with or decompose the starting materials and desired compound can be used in this invention. Suitable examples of the solvent which can be used include aliphatic hydrocarbons (e.g., hexane, heptane, petroleum ether, cyclohexane etc.), aromatic hydrocarbons (e.g., benzene, toluene, xylene, ethylbenzene, cumene, etc.), halogenated hydrocarbons (e.g., carbon tetrachloride, chloroform, dichloromethane, ethylene chloride, dichloropropane, trichloroethylene, tetrachloroethylene, chlorobenzene, etc.), ethers (e.g., diethyl ether, tetrahydrofuran, dioxane, etc.), ketones (e.g., acetone, methyl ethyl ketones, methyl isobutyl ketone, cyclohexanone, etc.), esters (e.g., ethyl acetate, etc.), nitriles (e.g., acetonitrile, etc.) and the like. These solvents can be used alone or in admixture.

The necessity of the promotor varies with a combination of the starting materials and the kind of solvent, but it is in general desired to use an organic or inorganic base. Suitable examples of the organic base which can be used include aliphatic or aromatic tertiary amines (e.g., triethylamine, pyridine, picoline, quinoline, etc.) and the like, and suitable examples of the inorganic base which can be used include alkali metal carbonates (e.g., sodium carbonate, potassium carbonate, etc.), alkali metal bicarbonates (e.g., sodium bicarbonate, potassium bicarbonate, etc.), alkali metal hydroxides (e.g., sodium hydroxide, potassium hydroxide, etc.), alkaline earth metal carbonates (e.g., calcium carbonate, etc.), alkaline earth metal hydroxides (e.g., calcium hydroxide, etc.) and the like.

Also, this reaction may be carried out by using water as the solvent. In this case, the inorganic base is dissolved therein together with the starting aminopyrazole, and the acid halide is added dropwise thereto whereby the mixture is allowed to react.

A molar proportion of the acid halide or acid anhydride to the aminopyrazole of the formula [II] is not restricted but in general can be used suitably in a range of from 1.0:1 to 1.2:1. In this case, when the amount of the latter is too large, then unreacted products remain, whereas when the amount of the former is too large, then the NH moiety on the pyrazole ring more likely reacts.

When the promoter is used, a suitable molar proportion thereof to the aminopyrazole of the formula [II] is in a range of from 1.0:1 to 2.0:1, preferably 1.0:1 to 1.2:1.

The reaction can be carried out at a temperature ranging from 0° C. to 150° C., but when water is used as the solvent, it is preferred to employ a low temperature of around 0° C.

A suitable time of the reaction is in a range of from 0.5 to 10 hours, preferably 1 to 5 hours.

The method of isolation of the desired product varies with the kinds of starting materials and solvent. For example, it can be isolated by a method in which after completion of the reaction, water or a diluted alkaline solution is added to the reaction mixture to form crystals which are then filtered and washed with water for recovery, or a method in which after completion of the reaction, water or a diluted alkaline solution is added to the reaction mixture, the mixture is shaken, and the organic layer is concentrated and subjected to crystallization from a solvent such as hexane, etc.

The compound of the formula [III] can be easily subjected to chlorination, bromination or nitration at the 4-position thereof by the use of respective reagents in a conventional method.

The chlorination can be carried out by reacting the compound of the formula [III] dissolved or suspended in a solvent with a chlorinating agent such as chlorine, sulfuryl chloride, etc. Examples of the solvent which can be used are those which do not react with the chlorinating agent, such as halogenated hydrocarbons, e.g., dichloromethane, carbon tetrachloride, chloroform, ethylene dichloride, dichloropropane, etc. The reaction temperature is suitably in a range of from 0° to 70° C. A suitable molar ratio of the chlorinating agent to the compound of the formula [III] is in a range of from 1.0:1 to 1.5:1, preferably from 1.0:1 to 1.3:1. The reaction time is suitably in a range of from 1 to 3 hours.

The chlorination can further be carried out in the following manner. In other words, the compound of the formula [III] is dissolved in hydrochloric acid, and a chloric acid salt such as sodium chlorate, potassium chlorate, etc. is added dropwise thereto, followed by allowing the mixture to react. After completion of the reaction, the reaction product is neutralized with an aqueous alkaline solution whereby the desired product is crystallized.

The bromination can be carried out by reacting the compound dissolved or suspended in a solvent with a brominating agent such as bromine, etc. Examples of the solvent which can be used are those which do not react with the brominating agent, such as chlorinated hydrocarbons, e.g., dichloromethane, carbon tetrachloride, chloroform, ethylene dichloride, dichloropropane, etc., acetic acid and the like. The reaction temperature is suitably in a range of from 0° to 60° C., and a suitable molar ratio of the brominating agent to the compound of the formula [III] is in a range of from 1.0:1 to 1.2:1.

The nitration can be carried out by applying a usual nitration method. For example, the compound of the formula [III] is dissolved in sulfuric acid or acetic anhydride, and fuming nitric acid is added dropwise thereto, whereby the mixture is allowed to react. The reaction temperature is suitably in a range of from 0° to 20° C. After completion of the reaction, the reaction product is poured into ice or ice water, and the resulting precipitate is collected by filtration to obtain the desired product.

The compound of the formula [I] which can be prepared by the respective reactions described above is, in general, sparingly soluble in water as well as benzene, toluene, carbon tetrachloride, chloroform, hexane, etc., but it is easily soluble in alcohols and acetone.

The aminopyrazole of the formula [II] which can be used as the starting material can be prepared by reacting cyanopinacoline and hydrazine in a solvent as illustrated in the following reaction scheme.

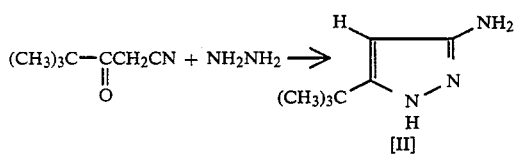

Examples of the solvent which can be used are those which do not react with the starting materials and desired product, such as alcohols, e.g., methanol, ethanol, etc. and the like. The reaction temperature is suitably in a range of from 30° to 100° C., and a suitable molar ratio of hydrazine to cyanopicoline is in a range of from 1.0:1 to 1.5:1. In the above reaction, cyanopinacoline which can be used as the starting material can be prepared by a method described by, for example, Ber., 44 2065(1911) or Japanese Patent Application (OPI) No. 137908/78.

The present invention is described in greater detail with reference to the following examples.

EXAMPLE 1

Preparation of 3-Amino-5-t-butylpyrazole 125 g (1 mole) of cyanopinacoline was dissolved in 200 ml of ethanol, and 55 g of hydrazine hydrate was added thereto, followed by heating the mixture under reflux conditions for 2 hours. After completion of the reaction, the ethanol was distilled off, and an alkaline solution was added to the residue. The mixture was extracted with 500 ml of benzene and dried over anhydrous sodium sulfate, followed by distilling off the benzene. The resulting residue was allowed to stand for solidification whereby 131 g of 3-amino-5-t-butylpyrazole was obtained.

EXAMPLE 2

Preparation of 5-t-Butyl-3-formylaminopyrazole

To 14 g (0.1 mole) of 3-amino-5-t-butylpyrazole prepared in Example 1 were added 16.3 g (0.3 mole) of 85% formic acid and 30 ml of toluene, followed by heating under reflux conditions while separating water by distillation. When a calculated amount of water and an excessive amount of formic acid distilled out, the heating was stopped. The reaction mixture was diluted with water and then concentrated as whole, whereby crystals were precipitated. The crystals were collected by filtration, washed with a sodium carbonate aqueous solution and water, and then dried to obtain 8.8 g of 5-t-butyl-3-formylaminopyrazole. This product was recrystallized from hydrous methanol and found to have a melting point of 204° to 206° C.

EXAMPLE 3

Preparation of 3-Acetylamino-5-t-butylpyrazole 42 g (0.3 mole) of 3-amino-5-t-butylpyrazole prepared in Example 1 was dissolved in 200 ml of benzene, and 30.6 g of acetic anhydride was added dropwise thereto at 20° to 40° C. while cooling with water. After completion of the dropwise addition, the mixture was allowed to react at 50° to 60° C. for 3 hours. Thereafter, the reaction product was cooled, and water was added to form a precipitate. The precipitate was collected by filtration, and washed with water and benzene to obtain 34 g of 3-acetylamino-5-t-butylpyrazole. This product was recrystallized from hydrous methanol and found to have a melting point of 194° to 195° C.

The identification of the product was carried out by means IR, NMR and mass analyses. The IR analysis showed the presence of characteristic absorption peaks for a >C=O bond and an N—H bond, respectively, thus the presence of an

bond could be estimated. Further, the NMR spectrum is shown in Table 1, and the mass analysis showed the presence of a molecular ion peak at 181.

EXAMPLE 4

Preparation of 5-t-Butyl-3-pivaloylaminopyrazole 100 g (0.72 mole) of 3-amino-5-t-butylpyrazole prepared in Example 1 was dissolved in 200 ml of benzene, and 134 g of pivalic anhydride was added thereto. The resulting mixture was heated at 60° C. for 3 hours. The reaction product was poured into a 10% sodium hydroxide aqueous solution under cooling and then stirred, whereby crystals were precipitated. The crystals were collected by filtration, washed with water and dried to obtain 103 g of 5-t-butyl-3-pivaloylaminopyrazole. This product was recrystallized from methanol and found to have a melting point of 209° to 210° C. The mass analysis showed the presence of a molecular ion peak at 223.

EXAMPLE 5

Preparation of 5-t-Butyl-3-propionylaminopyrazole 20 g (0.14 mole) of 3-amino-5-t-butylpyrazole prepared in Example 1 was dissolved in 100 ml of dioxane, and 14 g of propionyl chloride was added thereto. The mixture was allowed to react at 80° C. for 5 hours. After completion of the reaction, the dioxane was distilled off under reduced pressure, and then water was added to the residue whereby the reaction product was dissolved therein. The resulting solution was neutralized with a 10% sodium hydroxide aqueous solution whereby crystals were precipitated. The crystals were collected by filtration, washed with water and benzene, and then dried to obtain 22 g of 5-t-butyl-3-propionylaminopyrazole. This product was recrystallized from methanol and found to have a melting point of 228° to 229° C.

EXAMPLE 6

Preparation of 5-t-Butyl-3-isobutyroylaminopyrazole 60 g (0.43 mole) of 3-amino-5-t-butylpyrazole prepared in Example 1 was dissolved in 200 ml of benzene, and 68 g of isobutyric anhydride was added dropwise thereto at 20° C. while cooling with water. The mixture was further allowed to react at 60° C. for 3 hours. After completion of the reaction, a sodium carbonate aqueous solution was added to the reaction mixture with stirring whereby crystals were precipitated. The crystals were collected by filtration, washed with water and benzene, and then dried to obtain 60 g of 5-t-butyl-3-isobutyroylaminopyrazole. The mass analysis showed the presence of a molecular ion peak at 209.

EXAMPLE 7

Preparation of 5-t-Butyl-3-valerylaminopyrazole 5.6 g (0.04 mole) of 3-amino-5-t-butylpyrazole prepared in Example 1 was dissolved in 50 ml of acetone, and 4 g of sodium bicarbonate was suspended thereinto. To the suspension was added dropwise 3.7 g of valeryl chloride with stirring. After completion of the dropwise addition, the mixture was further allowed to react at 40° C. for 3 hours. Water was added to the reaction mixture, from which the reaction product was extracted with methylene chloride, followed by the concentration of methylene chloride solution. Thereafter, hexane was added thereto whereby crystals were precipitated. The crystals were collected by filtration and washed with water and benzene to obtain 2.3 g of 5-t-butyl-3-valerylaminopyrazole.

EXAMPLE 8

Preparation of 5-t-Butyl-3-monochloroacetylaminopyrazole 28 g (0.2 mole) of 3-amino-5-t-butylpyrazole prepared in Example 1 as dissolved in 200 ml of benzene, and 23 g of monochloroacetyl chloride was added dropwise thereto at 30° to 40° C. while cooling with water. After completion of the dropwise addition, the mixture was further allowed to react under reflux conditions for 5 hours. Thereafter, the resulting product was cooled and stirred whereby crystals were precipitated. The crystals were collected by filtration and washed with water and benzene to obtain 31 g of 5-t-butyl-3-monochloroacetylaminopyrazole.

EXAMPLE 9

Preparation of 5-t-Butyl-3-dichloroacetylaminopyrazole 4.2 g (0.03 mole) of 3-amino-5-t-butylpyrazole prepared in Example 1 and 3.1 g of triethylamine were dissolved in 30 ml of methylene chloride, and 4.4 g of dichloroacetyl chloride was added dropwise thereto at about 30° C. The resulting mixture was allowed to stand over night. Thereafter, water was added thereto whereby crystals were precipitated. The crystals were collected by filtration and washed with water to obtain 5.0 g of 5-t-butyl-3-dichloroacetylaminopyrazole.

EXAMPLE 10

Preparation of 5-t-Butyl-3-trichloroacetylaminopyrazole

The same procedure as in Example 9 was repeated except that 5.5 g of trichloroacetyl chloride was used in place of 4.4 g of dichloroacetyl chloride, to obtain 5.1 g of 5-t-butyl-3-trichloroacetylaminopyrazole.

EXAMPLE 11

Preparation of 5-t-Butyl-3-methacryloylaminopyrazole 4.2 g (0.03 mole) of 3-amino-5-t-butylpyrazole as prepared in Example 1 was dissolved in 50 ml of water, and 3.2 g of sodium carbonate was added thereto. To the resulting aqueous solution was added dropwise 3.2 g of methacryloyl chloride dissolved in 20 ml of carbon tetrachloride at 0° C. while cooling with ice for one hour. The reaction mixture was placed at room temperature (i.e., about 20° to 30° C.), followed by filtration and washing with water to obtain 3.6 g of 5-t-butyl-3-methacryloylaminopyrazole. The mass analysis showed the presence of a molecular ion peak at 207.

EXAMPLE 12

Preparation of 5-t-Butyl-3-(3'-butenoyl)aminopyrazole 4.2 g (0.03 mole) of 3-amino-5-t-butylpyrazole as prepared in Example 1 was dissolved in 50 ml of water, and 2.8 g of sodium bicarbonate was added thereto, followed by stirring the aqueous solution. Individually, 3.2 g of 3-butenoyl chloride was dissolved in 50 ml of carbon tetrachloride, and the resulting mixture was added dropwise to the abovedescribed aqueous solution at 5° to 10° C. while cooling with ice. The reaction mixture was placed at room temperature, followed by filtration and washing with water to obtain 2.6 g of 5-t-butyl-3-(3'-butenoyl)aminopyrazole.

EXAMPLE 13

Preparation of 5-t-Butyl-3-cyclopropanecarbonylaminopyrazole 7 g (0.05 mole) of 3-amino-5-t-butylpyrazole as prepared in Example 1 and 6 g of triethylamine were dissolved in 50 ml of methylene chloride. To this solution was added dropwise 5.7 g of cyclopropanecarboxylic acid chloride dissolved in 50 ml of carbon tetrachloride. The resulting mixture was allowed to stand over night. Thereafter, water was added thereto whereby crystals were precipitated. The crystals were collected by filtration and washed with water and carbon tetrachloride to obtain 5.3 g of 5-t-butyl-3-cyclopropanecarbonylaminopyrazole.

EXAMPLE 14

Preparation of 5-t-Butyl-3-cyclobutanecarbonylaminopyrazole 4.3 g (0.03 mole) of 3-amino-5-t-butylpyrazole as prepared in Example 1 and 3 g of triethylamine were dissolved in 30 ml of methylene chloride. To this solution was added dropwise 3.6 g of cyclobutanecarboxylic acid chloride dissolved in 30 ml of carbon tetrachloride. The resulting mixture was allowed to stand at room temperature over night. Thereafter, water was added thereto followed by shaking it. Crystals thus formed were collected by filtration and washed with water and carbon tetrachloride to obtain 5-t-butyl-3-cyclobutanecarbonylaminopyrazole.

EXAMPLE 15

Preparation of 5-t-Butyl-3-(2',2'-dimethylcyclopropanecarbonylamino)pyrazole 3.4 g (0.024 mole) of dimethylcyclopropanecarboxylic acid was dissolved in 30 ml of carbon tetrachloride, and 3.5 g of thionyl chloride was added thereto. The resulting mixture was allowed to react to prepare a solution of dimethylcyclopropanecarboxylic acid chloride.

Separately, 4.3 g of 3-amino-5-t-butylpyrazole as prepared in Example 1 and 5 ml of triethylamine were dissolved in 50 ml of methylene chloride. To this solution was added dropwise the solution prepared as above, followed by allowing to stand at room temperature over night. Thereafter, a potassium carbonate aqueous solution was added thereto, and the mixture was shaken. Crystals thus formed were collected by filtration, and washed with water and carbon tetrachloride to obtain 2.2 g of 5-t-butyl-3-(2',2'-dimethylcyclopropanecarbonylamino)pyrazole.

EXAMPLE 16

Preparation of 5-t-Butyl-3-(2',2'-dimethyl-4'-pentenoylamino)pyrazole 4.2 g (0.03 mole) of 3-amino-5-t-butylpyrazole as prepared in Example 1 and 5 ml of triethylamine were dissolved in 30 ml of methylene chloride. To this solution was added 4.4 g of 2,2-dimethyl-4-pentenoyl chloride, and the mixture was allowed to stand at room temperature over night. Thereafter, a sodium carbonate aqueous solution was added thereto followed by shaking. The organic layer was separated and concentrated. To the concentrate was added hexane to obtain 2.1 g of 5-t-butyl-3-(2',2'-dimethyl-4'-pentenoylamino)pyrazole.

EXAMPLE 17

Preparation of 5-t-Butyl-4-chloro-3-propionylaminopyrazole 5.8 g (0.03 mole) of 5-t-butyl-3-propionylaminopyrazole prepared in Example 5 was dispersed in 30 ml of chloroform, and the dispersion was stirred while adding dropwise thereto sulfuryl chloride. The mixture was further heated under reflux conditions for one hour, and the solvent was distilled off. To the residue was added a sodium bicarbonate aqueous solution whereby crystals were precipitated. The crystals were collected by filtration, washed with water and then dried to obtain 3.9 g of 5-t-butyl-4-chloro-3-propionylaminopyrazole. This product was recrystallized from hydrous methanol and found to have a melting point of 136° to 137° C.

EXAMPLE 18

Preparation of 5-t-Butyl-4-chloro-3-pivaloylaminopyrazole 9 g (0.04 mole) of 5-t-butyl-3-pivaloylaminopyrazole prepared in Example 4 was dissolved in 50 ml of concentrated hydrochloric acid, and 1.8 g of sodium chlorate dissolved in 40 ml of water was gradually added dropwise thereto. After completion of the reaction, the reaction product was neutralized with sodium hydroxide, and the solid thus formed was collected by filtration and dissolved in methanol. To the resulting solution was added water, whereby crystals were precipitated. The crystals were washed with water and dried to obtain 7.2 g of 5-t-butyl-4-chloro-3-pivaloylaminopyrazole. This product was recrystallized from hydrous methanol and found to have a melting point of 156° to 158° C.

EXAMPLE 19

Preparation of 5-t-Butyl-4-bromo-3-acetylaminopyrazole 4.5 g (0.025 mole) of 3-acetylamino-5-t-butylpyrazole prepared in Example 3 was dissolved in 20 ml of acetic acid, and 4.0 g of bromine was added dropwise thereto while stirring. The reaction solution was heated at 60° C. for one hour and then cooled. 50 ml of water was added to the resulting solution and allowed to stand, whereby crystals were precipitated. The crystals were collected by filtration, washed with water and then dried to obtain 5.2 g of 5-t-butyl-4-bromo-3-acetylaminopyrazole. This product was recrystallized from methanol and found to have a melting point of 234° to 235° C.

EXAMPLE 20

Preparation of 5-t-Butyl-4-nitro-3-propionylaminopyrazole 2 g (0.01 mole) of 5-t-butyl-3-propionylaminopyrazole as prepared in Example 5 was dissolved in 20 ml of concentrated sulfuric acid, and the solution was cooled to 0° C. 0.6 ml of fuming nitric acid was added dropwise thereto, and the mixture was allowed to react for one hour at 0° C. After completion of the reaction, the reaction solution was poured into a large amount of ice, whereby crystals were precipitated. The crystals were collected by filtration and washed with water to obtain 1 g of 5-t-butyl-4-nitro-3-propionylaminopyrazole.

The active compound according to this invention can be formulated into various formulations, e.g., emulsifiable concentrates, wettable powders, flowable formulations, dusts, granules, etc., by the application of a conventional manner for formulation.

Further, the compound of this invention can be mixed with other herbicides. Still further, in order to expand the scope of activity, the compound of this invention can be mixed with other pesticides than herbicides, such as plant growth regulators, insecticides, nematocides, fungicides, etc.

Typical formulations are explained by reference to the following Formulation Examples. In the formulation Examples, all parts are by weight.

FORMULATION EXAMPLE 1

Preparation of Wettable Powder 50 parts of, as an active ingredient, each compound as shown in Table 1, 10 parts of diatomaceous earth, 35 parts of clay, 3 parts of sodium polyoxyethylene alkylacryl ether sulfonate and 2 parts of sodium alkylnaphthalenesulfonate were mixed and pulverized to obtain a wettable powder having 50% of the active ingredient.

In the use thereof, the wettable powder is diluted with water to a predetermined concentration and then subjected to spraying.

FORMULATION EXAMPLE 2

Preparation of Granule 5 parts of, as an active ingredient, each compound as shown in Table 1, 20 parts of bentonite, 73 parts of clay and 2 parts of sodium dodecylbenzenesulfonate were subjected to intimate mixing, and about 20 parts of water was added thereto. The resulting mixture was kneaded by means of a kneader, and passed through a granulator to form granules. The thus formed granules were dried and controlled in particle size to obtain granules having 5% of the active ingredient.

FORMULATION EXAMPLE 3

Preparation of Emulsifiable Concentrate 15 parts of, as an active ingredient, each compound as shown in Table 1, 40 parts of dimethylacetamide, 40 parts of xylene and 5 parts of polyoxyethylene alkylaryl ether were mixed to form a homogeneous solution.

Thus, an emulsifiable concentrate having 15% of the active ingredient was obtained.

In the use thereof, the emulsifiable concentrate is diluted with water to a predetermined concentration and then subjected to spraying.

The acylaminopyrazole derivative represented by the formula [I] has an excellent herbicidal activity. Therefore, it is effective for controlling weeds growing in upland farms, orchards, non-caltivated fields, etc. When this active compound is applied on the surface of a soil or mixed with a soil, it can inhibit the growth of weeds and ultimately result in withering thereof. Further, it can control growing weeds by foliar application.

If the amount of the compound of this invention applied is chosen within a range of from 0.5 to 10 kg/ha, it can be used as a selective herbicide in cultivation fields for corn, wheat, barley, sugar beet, soybeans, peanut, sunflower, potato, cotton and fruits. Further, if the application amount is increased, the compound of this invention can be applied as a non-selective herbicide.

The compound of this invention can, for example, be used for controlling the following weeds:

(Triticum aestivum) and mung bean (Phaseolus radiatus) were sown in each pot, followed by covering with soil to a depth of about 5 mm. On the same day, a wettable powder containing each compound as shown in Table 2 was diluted with water and applied to the surface of the soil in each pot in an amount of active ingredient as shown in Table 2. The herbicidal activity was visually evaluated two weeks after the application. The results obtained are shown in Table 2. Ratings of growth inhibition shown in Table 2 were given on a scale of 0–5 grades in which the grade 5 indicates a complete kill of the plant and the grade 0 indicates no inhibition.

5 = Complete kill
4 = 80–99% Damage
3 = 60–79% Damage
2 = 40–59% Damage
1 = 20–39% Damage
0 = 0–19% Damage

Dicotyledon

| | |
|---|---|
| Abtilon theophrasti (velvetleaf), | Amaranthus retroflexus (pigweed), |
| Ambrosia artemisiifolia (ragweed), | Aster sublatus (aster), |
| Bidens pilosa (beggarticks), | Calonyction muricatum (moonflower), |
| Capsella bursa-pastoris (shepherdspurse), | Cassis obtusifolia (sicklepod), |
| Chenopodium album (lambsquaters), | Convolvulus arvensis (field bindweed), |
| Datura stramonium (jimsonweed), | Galium aparine (bedstraw), |
| Ipomea purpurea (morningglory), | Lamium amplexicaule (hembit), |
| Lepidium virginicum (pepperwood) | Oxalis corniculata (woodsorrel), |
| Polygonum spp. (smartweed), | Portulaca oleracea (purslane), |
| Rananculus repens (buttercup) | Rorippa indica (fieldcress), |
| Sagina japonica (pearlwort), | Senecio vulgaris (groundsel), |
| Sesbania exaltata (coffeebeen), | Sida spinosa (pricky sida), |
| Solanium nigrum (nightshade) | Sunchus asper (spiny sowthistle), |
| Sterallia midia (chickweed), | Vicia sativa (vetch), |
| Xanthium pensylvanicum (cocklebur) | |

Monocotyledon

| | |
|---|---|
| Agropyron repens (quackgrass), | Alopeculus pratensis (meadow foxtail), |
| Avena fatus (wild oat), | Digitaria sanguinalis (crabgrass) |
| Echinochloa crusgalli (barnyardgrass), | Eleusine indica (goosegrass), |
| Lorium multiflorum (Italian ryegrass), | Panicum dichotomiflorum (fall panicium), |
| Poa anua (bluegrass), | Polygonum convulvulus (buckwheat) |
| Setaria faberii (giant foxtail), | Setaria viridis (green foxtail), |
| Sorghum halepens (Johnsongrass) | |

Perennial weeds

| | |
|---|---|
| Cyperus iria (flatsedge), | Kyllinga brevifolia (kyllinga) |

As described above, the compound of this invention has an excellent herbicidal activity against a wide range of weeds, and especially, it can exhibit a markedly high herbicidal activity when applied to the surface of a soil or to the foliar portions of weeds before or after the germination of the weeds.

Fruther, when the compound of this invention is mixed with soil, it can also exhibit a quite high herbicidal activity.

In order to explain the herbicidal activity of the compounds of the present invention, a series of Test Examples are shown.

TEST EXAMPLE 1

Pre-Emergence Soil Treatment

Pots of 100 cm² were packed with volcanic ash soil and predetermined amounts of seeds of crabgrass (Digitaria sanguinalis), edible barnyardgrass (Echinochloa crus-galli), smartweed (Polygonum nodosum), pigweed (Amaranthus retroflexus), corn (Zea mays), wheat

TABLE 2

| Compound No. | Dosage (kg/ha) | A | B | C | D | E | F | G |
|---|---|---|---|---|---|---|---|---|
| 5 | 10 | 0 | 0 | 5 | 4 | 0 | 0 | 0 |
| 6 | 10 | 5 | 3 | 5 | 5 | 0 | 4.5 | 0 |
|   | 2.5 | 2 | 0 | 2 | 3 | 0 | 0 | 0 |
| 8 | 10 | 4.5 | 4 | 5 | 5 | 2 | 3 | 0 |
| 9 | 10 | 0 | 0 | 4 | 5 | 0 | 0 | 0 |
|   | 2.5 | 0 | 0 | 3 | 4 | 0 | 0 | 0 |
| 11 | 10 | 5 | 5 | 5 | 5 | 3 | 5 | 5 |
|   | 2.5 | 4.5 | 1 | 5 | 5 | 0 | 5 | 5 |
| 14 | 10 | 5 | 2 | 5 | 5 | 1 | 5 | 5 |
|   | 2.5 | 5 | 0 | 0 | 5 | 0 | 0 | 0 |
| 15 | 10 | 5 | 5 | 5 | 5 | 5 | 5 | 5 |
|   | 2.5 | 5 | 5 | 5 | 5 | 1 | 5 | 5 |
| 16 | 10 | 3 | 5 | 5 | 5 | 4 | 5 | 4 |
|   | 2.5 | 0 | 2 | 5 | 5 | 0 | 5 | 0 |
| 17 | 10 | 5 | 5 | 5 | 5 | 5 | 5 | 5 |
|   | 2.5 | 5 | 5 | 5 | 5 | 4 | 4.5 | 5 |
| 18 | 10 | 5 | 5 | 5 | 5 | 4.5 | 5 | 5 |
|   | 2.5 | 5 | 5 | 5 | 5 | 1 | 5 | 0 |
| 19 | 10 | 5 | 5 | 5 | 5 | 4.5 | 5 | 5 |
|   | 2.5 | 5 | 5 | 5 | 5 | 0 | 5 | 0 |
| 20 | 10 | 5 | 5 | 5 | 5 | 1 | 5 | 4 |
|   | 2.5 | 4 | 3 | 4 | 2 | 0 | 0 | 0 |
| 21 | 10 | 5 | 5 | 5 | 5 | 3 | 5 | 5 |
|   | 2.5 | 5 | 4.5 | 5 | 5 | 3 | 2 | 5 |
| 22 | 10 | 5 | 5 | 5 | 5 | 2 | 5 | 5 |

TABLE 2-continued

| Compound No. | Dosage (kg/ha) | Herbicidal Activity | | | | | | |
|---|---|---|---|---|---|---|---|---|
| | | A | B | C | D | E | F | G |
| | 2.5 | 5 | 2 | 5 | 5 | 0 | 2 | 0 |
| 23 | 10 | 5 | 5 | 5 | 5 | 0 | 5 | 5 |
| | 2.5 | 4 | 3 | 5 | 4.5 | 0 | 0 | 0 |
| 24 | 10 | 2 | 0 | 5 | 0 | 0 | 0 | 0 |
| | 2.5 | 0 | 0 | 2 | 0 | 0 | 0 | 0 |
| 25 | 10 | 5 | 5 | 5 | 4 | 1 | 2 | 0 |
| | 2.5 | 5 | 0 | 0 | 0 | 0 | 0 | 0 |
| 26 | 10 | 5 | 5 | 5 | 5 | 5 | 5 | 5 |
| | 2.5 | 5 | 5 | 5 | 5 | 1 | 5 | 0 |
| 27 | 10 | 5 | 5 | 5 | 5 | 5 | 5 | 5 |
| | 2.5 | 5 | 5 | 5 | 5 | 5 | 5 | 5 |
| 28 | 10 | 5 | 5 | 5 | 5 | 3 | 4 | 5 |
| | 2.5 | 4.5 | 1 | 5 | 5 | 0 | 1 | 5 |
| 29 | 10 | 1 | 0 | 5 | 5 | 0 | 0 | 0 |
| 30 | 10 | 5 | 4 | 5 | 5 | 0 | 0 | 2 |
| | 2.5 | 2 | 2 | 5 | 5 | 0 | 0 | 0 |
| 33 | 10 | 4.5 | 4.5 | 0 | 0 | 4 | 5 | 0 |
| | 2.5 | 2 | 3 | 0 | 0 | 0 | 4 | 0 |
| 34 | 10 | 2 | 3 | 0 | 0 | 3 | 4 | 0 |
| 35 | 10 | 5 | 4 | 5 | 5 | 0 | 0 | 5 |
| 36 | 10 | 4 | 3 | 5 | 5 | 2 | 2 | 0 |
| | 2.5 | 2 | 0 | 3 | 4 | 0 | 0 | 0 |
| 38 | 10 | 5 | 4 | 5 | 5 | 4 | 5 | 5 |
| | 2.5 | 1 | 0 | 5 | 3 | 0 | 0 | 0 |
| 39 | 10 | 4 | 4 | 5 | 5 | 1 | 2 | 3 |
| | 2.5 | 0 | 0 | 0 | 5 | 0 | 0 | 0 |
| 40 | 10 | 0 | 0 | 4 | 4.5 | 5 | 0 | 0 |
| 42 | 10 | 5 | 5 | 5 | 5 | 4.5 | 4.5 | 5 |
| | 2.5 | 1 | 0 | 4 | 2 | 0 | 0 | 0 |
| 43 | 10 | 0 | 0 | 4 | 4 | 0 | 0 | 5 |

A: Crabgrass (*Digitaria sanguinalis*)
B: Edible Barnyardgrass (*Echinochloa crus-galli*)
C: Smartweed (*Polygonum nodosum*)
D: Pigweed (*Amaranthus retroflexus*)
E: Corn (*Zea mays*)
F: Wheat (*Triticum aestivum*)
G: Mung Bean (*Phaseolus radiatus*)

TEST EXAMPLE 2

Foliar Spary (Post-Emergence) Treatment

Ceramic pots of 100 cm² were packed with volcanic ash soil and predetermined amounts of seeds of crabgrass (Digitaria sanguinalis), edible barnyardgrass (Echinochloa crus-galli), smartweed (Polygonum nodosum), pigweed (Amaranthus retroflexus), corn (Zea mays), wheat (Triticum aestivum) and mung bean (Phaseolus radiatus) were sown, followed by covering with soil to a depth of about 1 cm. The resulting pots were allowed to stand in a green house. When the respective plants grew up to a 1–2 leaf stage, a wettable powder containing each compound as shown in Table 3 was diluted with water and applied foliarly to the plants by means of a sprayer in an amount of active ingredient as shown in Table 3. Ten days after the application, the herbicidal activity was visually evaluated on the same scale as in Test Example 1. The results obtained are shown in Table 3.

TABLE 3

| Compound No. | Dosage (kg/ha) | Herbicidal Activity | | | | | | |
|---|---|---|---|---|---|---|---|---|
| | | A | B | C | D | E | F | G |
| 1 | 10 | 2 | 2 | 5 | 5 | 0 | 1 | 5 |
| | 2.5 | 0 | 0 | 3 | 4 | 0 | 0 | 0 |
| 2 | 10 | 2 | 3 | 5 | 5 | 3 | 3 | 5 |
| | 2 | 0 | 5 | 5 | 0 | 1 | 5 | |
| 4 | 10 | 0 | 0 | 5 | 5 | 1 | 1 | 5 |
| 5 | 10 | 5 | 2 | 5 | 5 | 1 | 0 | 4.5 |
| 6 | 10 | 5 | 5 | 5 | 5 | 4 | 5 | 5 |
| | 2.5 | 4 | 3 | 5 | 5 | 0 | 1 | 5 |
| 7 | 10 | 3 | 3 | 5 | 3 | 5 | 3 | 5 |
| | 2.5 | 2 | 3 | 5 | 3 | 5 | 3 | 4 |
| 8 | 10 | 3 | 3 | 5 | 5 | 0 | 4 | 5 |
| | 2.5 | 4 | 0 | 4 | 4 | 0 | 0 | 5 |
| 9 | 10 | 4.5 | 4 | 4 | 4 | 1 | 0 | 5 |
| | 2.5 | 1 | 2 | 5 | 4 | 0 | 0 | 4 |
| 10 | 10 | 3 | 2 | 5 | 5 | 1 | 2 | 5 |
| 11 | 10 | 3 | 5 | 5 | 5 | 5 | 5 | 5 |
| | 2.5 | 3 | 2 | 5 | 4 | 1 | 3 | 5 |
| 12 | 10 | 4 | 4 | 5 | 5 | 2 | 4 | 5 |
| 13 | 10 | 2 | 2 | 5 | 4 | 4 | 4 | 5 |
| | 2.5 | 0 | 0 | 0 | 0 | 1 | 0 | 3 |
| 14 | 10 | 5 | 5 | 5 | 5 | 3 | 5 | 5 |
| | 2.5 | 4 | 0 | 5 | 5 | 0 | 3 | 1 |
| 15 | 10 | 2 | 3 | 4 | 4 | 4 | 4 | 5 |
| | 2.5 | 0 | 0 | 2 | 3 | 0 | 0 | 3 |
| 17 | 10 | 5 | 5 | 5 | 5 | 5 | 5 | 5 |
| | 2.5 | 5 | 5 | 5 | 5 | 3 | 3 | 5 |
| 18 | 10 | 5 | 5 | 5 | 5 | 5 | 5 | 5 |
| | 2.5 | 2 | 1 | 5 | 5 | 0 | 3 | 2 |
| 19 | 10 | 5 | 5 | 5 | 5 | 5 | 5 | 5 |
| | 2.5 | 4 | 3 | 5 | 5 | 2 | 4 | 5 |
| 20 | 10 | 5 | 5 | 5 | 5 | 1 | 3 | 5 |
| | 2.5 | 5 | 5 | 5 | 5 | 0 | 1 | 5 |
| 21 | 10 | 5 | 5 | 5 | 5 | 5 | 5 | 5 |
| | 2.5 | 5 | 5 | 5 | 5 | 0 | 4 | 5 |
| 22 | 10 | 5 | 5 | 5 | 5 | 3 | 5 | 5 |
| | 2.5 | 2 | 0 | 5 | 5 | 0 | 0 | 5 |
| 23 | 10 | 5 | 5 | 5 | 5 | 5 | 5 | 5 |
| | 2.5 | 5 | 3 | 5 | 5 | 1 | 1 | 5 |
| 24 | 10 | 0 | 0 | 5 | 5 | 0 | 0 | 4 |
| 25 | 10 | 5 | 4 | 5 | 5 | 4 | 4 | 5 |
| | 2.5 | 0 | 2 | 5 | 5 | 1 | 1 | 3 |
| 26 | 10 | 5 | 5 | 5 | 5 | 5 | 5 | 5 |
| | 2.5 | 5 | 4.5 | 5 | 5 | 4.5 | 5 | 5 |
| 27 | 10 | 5 | 5 | 5 | 5 | 5 | 5 | 5 |
| | 2.5 | 5 | 5 | 5 | 5 | 5 | 5 | 5 |
| 28 | 10 | 5 | 5 | 5 | 5 | 4 | 5 | 5 |
| | 2.5 | 2 | 3 | 5 | 5 | 0 | 0 | 4 |
| 29 | 10 | 0 | 2 | 2 | 1 | 0 | 0 | 0 |
| 30 | 10 | 3 | 1 | 5 | 5 | 1 | 2 | 5 |
| | 2.5 | 0 | 0 | 2 | 2 | 0 | 0 | 0 |
| 31 | 10 | 2 | 0 | 5 | 2 | 0 | 0 | 5 |
| 32 | 10 | 4.5 | 3 | 5 | 5 | 3 | 2 | 3 |
| | 2.5 | 0 | 0 | 2 | 2 | 0 | 0 | 0 |
| 33 | 10 | 0 | 0 | 4 | 5 | 0 | 0 | 0 |
| 34 | 10 | 5 | 5 | 5 | 5 | 5 | 5 | 5 |
| | 2.5 | 2 | 4 | 2 | 2 | 4 | 3 | 4 |
| 35 | 10 | 5 | 5 | 5 | 5 | 3 | 4 | 5 |
| | 2.5 | 3 | 0 | 5 | 5 | 0 | 2 | 5 |
| 36 | 10 | 5 | 5 | 5 | 5 | 2 | 5 | 5 |
| | 2.5 | 5 | 0 | 5 | 5 | 1 | 1 | 5 |
| 37 | 10 | 1 | 1 | 2 | 0 | 0 | 1 | 5 |
| 38 | 10 | 4 | 4 | 5 | 5 | 4.5 | 5 | 5 |
| | 2.5 | 3 | 4 | 4 | 5 | 2 | 3 | 5 |
| 39 | 10 | 4 | 3 | 5 | 5 | 3 | 5 | 5 |
| | 2.5 | 1 | 0 | 3 | 2 | 0 | 0 | 0 |
| 41 | 10 | 5 | 3 | 5 | 5 | 4 | 5 | 5 |
| | 2.5 | 0 | 0 | 4 | 5 | 0 | 0 | 5 |
| 42 | 10 | 5 | 5 | 5 | 5 | 5 | 4 | 5 |
| | 2.5 | 2 | 3 | 5 | 5 | 2 | 1 | 3 |
| 43 | 10 | 2 | 2 | 4 | 5 | 1 | 1 | 5 |
| | 2.5 | 0 | 0 | 2 | 3 | 0 | 0 | 0 |

A: Crabgrass (*Digitaria sanguinalis*)
B: Edible Barnyardgrass (*Echinochloa crus-galli*)
C: Smartweed (*Polygonum nodosum*)
D: Pigweed (*Amaranthus retroflexus*)
E: Corn (*Zea mays*)
F: Wheat (*Triticum aestivum*)
G: Mung Bean (*Phaseolus radiatus*)

TEST EXAMPLE 3

Pre-Emergence Treatment in Paddy Condition

Ceramic pots of 120 cm² were packed with paddy soil and predetermined amounts of seeds of barnyardgrass (Echinochloa crus-galli) and pickerelweed (Monochoria vaginalis) were sown to a depth of about 2 cm from the surface layer. Two tubers of slender spikerush (Eleocharis acicularis) and two rice plants having a 2-leaf stage were transplanted respectively into each pot, and the depth of water was maintained at about 3 cm. Three days later, a wettable powder containing each compound as shown in Table 4 prepared in the same manner as in Formulation 1 was administered to water in an amount of active ingredient as shown in Table 4. Three weeks after the treatment, the ratings of growth of the plants were visually evaluated on the same scale as in Test Example 1. The results obtained are shown in Table 4.

TABLE 4

| Compound No. | Dosage (kg/ha) | Herbicidal Activity | | | |
|---|---|---|---|---|---|
| | | A | B | C | D |
| 1 | 10 | 4 | 0 | 0 | 0 |
| 2 | 10 | 2 | 2 | 0 | 3 |
| | 2.5 | 0 | 0 | 0 | 1 |
| 4 | 10 | 2 | 0 | 0 | 0 |
| 5 | 10 | 4 | 3 | 5 | 4 |
| 6 | 10 | 4 | 3 | 2 | 4 |
| | 2.5 | 1 | 3 | 0 | 3 |
| 7 | 10 | 3 | 0 | 0 | 0 |
| 9 | 10 | 4 | 3 | 1 | 5 |
| | 2.5 | 1 | 0 | 0 | 1 |
| 10 | 10 | 3 | 3 | 0 | 5 |
| | 2.5 | 0 | 0 | 0 | 4 |
| 11 | 10 | 5 | 4 | 5 | 5 |
| | 2.5 | 4 | 3 | 4 | 5 |
| 12 | 10 | 2 | 0 | 0 | 5 |
| 13 | 10 | 4.5 | — | 4 | 4 |
| | 2.5 | 2 | — | 0 | 3 |
| 14 | 10 | 4 | 3 | 2 | 5 |
| | 2.5 | 3 | 0 | 0 | 4 |
| 15 | 10 | 5 | 5 | 5 | 5 |
| | 2.5 | 4 | 3 | 4.5 | 5 |
| 16 | 10 | 2 | 0 | 2 | 4 |
| | 2.5 | 0 | 0 | 0 | 3 |
| 17 | 10 | 5 | 4.5 | 5 | 5 |
| | 2.5 | 5 | 2 | 5 | 5 |
| 18 | 10 | 5 | 3 | 5 | 5 |
| | 2.5 | 4 | 0 | 3 | 4.5 |
| 19 | 10 | 5 | 5 | 5 | 5 |
| | 2.5 | 5 | 0 | 5 | 5 |
| 20 | 10 | 5 | 5 | 5 | 5 |
| | 2.5 | 5 | 4.5 | 5 | 5 |
| 21 | 10 | 5 | 5 | 5 | 5 |
| | 2.5 | 5 | 4 | 5 | 5 |
| 22 | 10 | 5 | 5 | 4.5 | 5 |
| | 2.5 | 4.5 | 4 | 4 | 5 |
| 23 | 10 | 5 | 4 | 5 | 5 |
| | 2.5 | 5 | 2 | 5 | 5 |
| 24 | 10 | 4 | 0 | 0 | 5 |
| | 2.5 | 1 | 0 | 0 | 2 |
| 25 | 10 | 5 | 4 | 5 | 5 |
| | 2.5 | 4 | 2 | 5 | 4.5 |
| 26 | 10 | 5 | 4.5 | 5 | 5 |
| | 2.5 | 5 | 4 | 5 | 5 |
| 27 | 10 | 5 | 4.5 | 5 | 5 |
| | 2.5 | 4.5 | 4.5 | 5 | 5 |
| 28 | 10 | 5 | 4 | 5 | 5 |
| | 2.5 | 5 | 3 | 5 | 5 |
| 29 | 10 | 4 | 3 | 5 | 0 |
| 30 | 10 | 4.5 | 3 | 4 | 5 |
| | 2.5 | 3 | 2 | 2 | 4 |
| 32 | 10 | 0 | 3 | 5 | 4 |
| | 2.5 | 0 | 0 | 2 | 1 |
| 33 | 10 | 5 | 3 | 3 | 1 |
| | 2.5 | 5 | 2 | 2 | 0 |
| 34 | 10 | 0 | — | 3 | 3 |
| | 2.5 | 0 | — | 0 | 2 |
| 35 | 10 | 5 | 3 | 5 | 5 |
| | 2.5 | 5 | 3 | 5 | 5 |
| 36 | 10 | 5 | 3 | 4 | 5 |
| | 2.5 | 2 | 2 | 3 | 5 |
| 37 | 10 | 0 | 0 | 2 | 3 |
| | 2.5 | — | — | — | 3 |
| 38 | 10 | 5 | 0 | 5 | 5 |
| | 2.5 | 3 | 0 | 2 | 3 |
| 39 | 10 | 5 | 2 | 5 | 5 |
| | 2.5 | 2 | 0 | 5 | 1 |
| 40 | 10 | 4.5 | — | 5 | 4 |

TABLE 4-continued

| Compound No. | Dosage (kg/ha) | Herbicidal Activity | | | |
|---|---|---|---|---|---|
| | | A | B | C | D |
| | 2.5 | 3 | — | 5 | 2 |
| 41 | 10 | 4 | — | 1 | 2 |
| | 2.5 | 3 | — | 0 | 4 |
| 42 | 10 | 5 | 5 | 5 | 5 |
| | 2.5 | 5 | 4 | 4 | 5 |
| 43 | 10 | 3 | 0 | 5 | 2 |
| | 2.5 | 2 | 0 | 0 | 3 |

A: Barnyard grass (*Echinochloa crus-galli*)
B: Pickerelweed (*Monochoria vaginalis*)
C: Slender Spikerush (*Eleocharis acicularis*)
D: Rice Plant As is clear from Table 4 above, the compounds according to this invention are effective for controlling the weeds that are serious weeds in the paddy field. Some of the compounds of this invention, however, had adverse effect to the rice plant.

While the invention has been described in detail and with reference to specific embodiment thereof, it will be apparent to one skilled in the art that various changes and modifications can be made therein without departing from the spirit and scope thereof.

What is claimed is:

1. A pyrazole derivative represented by Formula I:

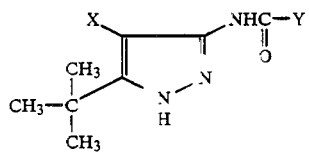

wherein X is a hydrogen atom and wherein Y is a straight or branched chain alkyl group having 1 to 10 carbon atoms, which may be substituted with halogen atoms or an alkoxy group; a straight or branched chain alkenyl group having 2 to 8 carbon atoms; a cycloalkyl group having 3 to 6 carbon atoms, which may be substituted with halogen atoms or lower alkyl groups; a phenyl lower alkyl group having 7 to 8 carbon atoms; or a

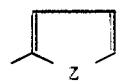

group wherein Z is an oxygen atom or a sulfur atom.

2. The pyrazole derivative as in claim 1 wherein Y is a phenyl lower alkyl group having 7 to 8 carbon atoms.

3. A pyrazole derivative represented by Formula I:

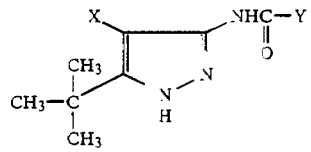

wherein X is a hydrogen atom and Y is $-C(CH_3)_2C_2H_5$.

4. A pyrazole derivative represented by Formula I:

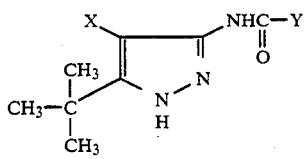

wherein X is a hydrogen atom and Y is —C₄H₉-tert.

5. A pyrazole derivative represented by Formula I:

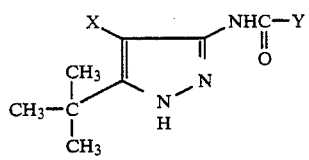

wherein X is a hydrogen atom and Y is —C(CH₃)₂C₃H₇-iso.

6. A pyrazole derivative represented by Formula I:

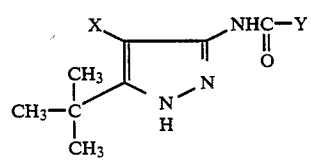

wherein x is a hydrogen atom and Y is —C(CH₃)₂C₃H₇—n.

7. A pyrazole derivative represented by Formula I:

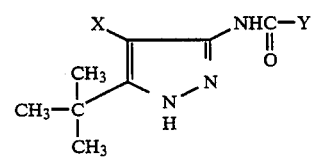

wherein X is a hydrogen atom and Y is —C(CH₃)₂C-H₂—CH=CH₂.

8. A pyrazole derivative represented by Formula I:

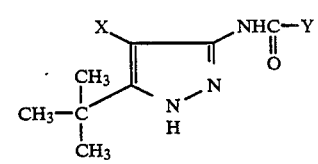

wherein X is a hydrogen atom and Y is

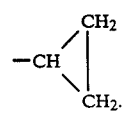

9. A herbicide composition represented by Formula I:

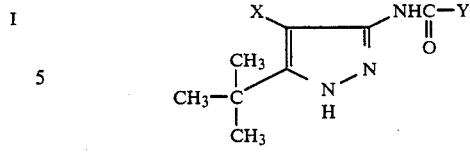

wherein X is a hydrogen atom and wherein Y is a straight or branched chain alkyl group having 1 to 10 carbon atoms, which may be substituted with halogen atoms or an alkoxy group; a straight or branched chain alkenyl group having 2 to 8 carbon atoms; a cycloalkyl group having 3 to 6 carbon atoms, which may be substituted with halogen atoms or lower alkyl groups; a phenyl lower alkyl group having 7 to 8 carbon atoms; or a

group wherein Z is an oxygen atom or a sulfur atom; and a carrier or diluent.

10. The herbicide composition as in claim 9 wherein Y is a phenyl lower alkyl group having 7 to 8 carbon atoms.

11. A herbicide composition comprising a herbicidally effective amount of a pyrazole derivative represented by Formula I:

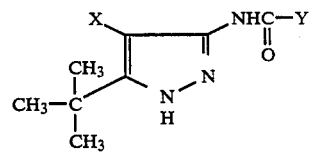

wherein X is a hydrogen atom and Y is —C(CH₃)₂C₂H₅ and a carrier.

12. A herbicide composition comprising a herbicidally effective amount of a pyrazole derivative represented by Formula I:

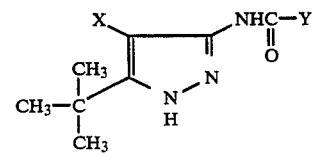

wherein X is a hydrogen atom and Y is —C₄H₉-tert and a carrier.

13. A herbicide composition comprising a herbicidally effective amount of a pyrazole derivative represented by Formula I:

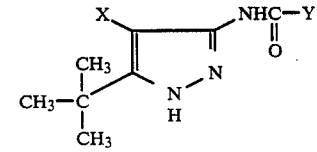

wherein X is a hydrogen atom and Y is —C(CH₃)₂C₃H₇-iso and a carrier.

14. A herbicide composition comprising a herbicidally effective amount of a pyrazole derivative represented by Formula I:

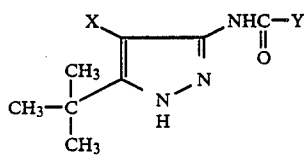  I wherein X is a hydrogen atom and Y is —C(CH$_3$)$_2$C$_3$H$_7$—n and a carrier.

15. A herbicide composition comprising a herbicidally effective amount of a pyrazole derivative represented by Formula I:

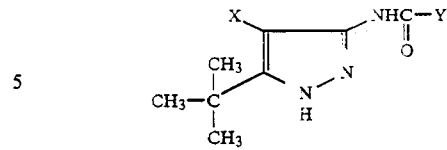

wherein X is a hydrogen atom and Y is —C(CH$_3$)$_2$CH$_2$.CH=CH$_2$ and a carrier.

16. A herbicide composition comprising a herbicidally effective amount of a pyrazole derivative represented by Formula I:

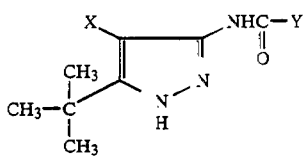

wherein X is a hydrogen atom and Y is

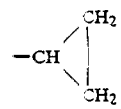

and a carrier.

* * * * *